(12) United States Patent
Chen et al.

(10) Patent No.: US 11,096,695 B2
(45) Date of Patent: *Aug. 24, 2021

(54) CIRCULAR STAPLER AND STAPLE HEAD ASSEMBLY THEREOF

(71) Applicant: Touchstone International Medical Science Co., Ltd., Suzhou (CN)

(72) Inventors: Wangdong Chen, Suzhou (CN); Kenzhan Sun, Suzhou (CN)

(73) Assignee: TOUCHSTONE INTERNATIONAL MEDICAL SCIENCE CO., LTD., Suzhou (CN)

( * ) Notice: Subject to any disclaimer, the term of this patent is extended or adjusted under 35 U.S.C. 154(b) by 24 days.

This patent is subject to a terminal disclaimer.

(21) Appl. No.: 16/553,756

(22) Filed: Aug. 28, 2019

(65) Prior Publication Data

US 2019/0380714 A1 Dec. 19, 2019

Related U.S. Application Data

(63) Continuation of application No. 14/655,350, filed as application No. PCT/CN2013/090676 on Dec. 27, 2013, now Pat. No. 10,433,848.

(30) Foreign Application Priority Data

Dec. 29, 2012 (CN) .......................... 201220755800.0
Dec. 29, 2012 (CN) .......................... 201220755812.3

(51) Int. Cl.
*A61B 17/115* (2006.01)
*A61B 17/068* (2006.01)

(Continued)

(52) U.S. Cl.
CPC ........ *A61B 17/1155* (2013.01); *A61B 17/068* (2013.01); *A61B 17/105* (2013.01);
(Continued)

(58) Field of Classification Search
CPC .... A61B 17/1155; A61B 17/08; A61B 17/105
See application file for complete search history.

(56) References Cited

U.S. PATENT DOCUMENTS

| 4,379,457 A | 4/1983 | Gravener et al. |
| 4,603,693 A | 8/1986 | Conta et al. |

(Continued)

FOREIGN PATENT DOCUMENTS

| CN | 2719237 Y | 8/2005 |
| CN | 101332102 A | 12/2008 |

(Continued)

*Primary Examiner* — Nathaniel C Chukwurah
*Assistant Examiner* — Lucas E. A. Palmer
(74) *Attorney, Agent, or Firm* — Fox Rothschild LLP

(57) ABSTRACT

A circular stapler and a staple head assembly thereof are disclosed. The staple head assembly comprises a staple barrel assembly and an anvil assembly. The anvil assembly includes an anvil ring and an anvil shaft which are fixedly connected to each other, where the anvil shaft is capable of sliding along the longitudinal direction in an expansion-stopping tube. The staple barrel assembly includes a staple barrel, a staple pusher piece arranged within the staple barrel and a staple cartridge fixed at a distal end of the staple barrel.

15 Claims, 15 Drawing Sheets

(51) Int. Cl.
*A61B 17/10* (2006.01)
*A61B 90/00* (2016.01)
*A61B 17/00* (2006.01)

(52) U.S. Cl.
CPC ........... *A61B 2017/00349* (2013.01); *A61B 2090/0811* (2016.02)

(56) References Cited

U.S. PATENT DOCUMENTS

| | | | |
|---|---|---|---|
| 4,606,343 A | 8/1986 | Conta et al. | |
| 5,119,983 A | 6/1992 | Green et al. | |
| 5,158,222 A | 10/1992 | Green et al. | |
| 5,205,459 A * | 4/1993 | Brinkerhoff | A61B 17/115 227/179.1 |
| 5,392,979 A * | 2/1995 | Green | A61B 17/115 227/179.1 |
| 5,522,534 A | 6/1996 | Viola et al. | |
| 5,637,097 A | 6/1997 | Yoon | |
| 5,860,581 A | 1/1999 | Robertson et al. | |
| 6,083,241 A * | 7/2000 | Longo | A61B 17/0293 227/179.1 |
| 6,102,271 A * | 8/2000 | Longo | A61B 17/0293 227/175.1 |
| 7,364,060 B2 * | 4/2008 | Milliman | A61B 17/068 227/175.1 |
| 8,231,042 B2 * | 7/2012 | Hessler | A61B 17/068 227/179.1 |
| 8,267,301 B2 | 9/2012 | Milliman et al. | |
| 8,281,974 B2 | 10/2012 | Hessler et al. | |
| 8,758,398 B2 | 6/2014 | Carley | |
| 8,875,974 B2 | 11/2014 | Rebuffat et al. | |
| 8,919,630 B2 | 12/2014 | Milliman | |
| 9,055,942 B2 * | 6/2015 | Balbierz | A61F 5/0036 |
| 9,204,789 B2 | 12/2015 | Wenchell et al. | |
| 9,327,097 B2 | 5/2016 | Ahluwalia | |
| 9,610,099 B2 | 4/2017 | Jones et al. | |
| 9,629,624 B2 | 4/2017 | Hessler et al. | |
| 9,757,133 B2 | 9/2017 | Latimer et al. | |
| 9,770,242 B2 | 9/2017 | Li et al. | |
| 9,826,979 B2 | 11/2017 | Chen et al. | |
| 2002/0063143 A1 | 5/2002 | Adams et al. | |
| 2005/0059996 A1 | 3/2005 | Bauman et al. | |
| 2005/0228414 A1 | 10/2005 | Mayoral | |
| 2008/0021500 A1 * | 1/2008 | Shifrin | A61B 17/115 606/219 |
| 2009/0001127 A1 * | 1/2009 | Chen | A61B 17/115 227/179.1 |
| 2009/0056515 A1 | 3/2009 | Viola et al. | |
| 2010/0089971 A1 | 4/2010 | Milliman et al. | |
| 2012/0292366 A1 | 11/2012 | Nalagatla et al. | |
| 2012/0292371 A1 | 11/2012 | Nalagatla et al. | |
| 2013/0181035 A1 * | 7/2013 | Milliman | A61B 17/068 227/180.1 |
| 2013/0267968 A1 | 10/2013 | Ferlin | |
| 2013/0289585 A1 | 10/2013 | Jones et al. | |
| 2014/0046352 A1 * | 2/2014 | Reboa | A61B 17/068 606/153 |
| 2014/0191012 A1 | 7/2014 | Chen et al. | |
| 2014/0374465 A1 | 12/2014 | Cole et al. | |
| 2015/0083778 A1 | 3/2015 | Li et al. | |
| 2015/0129636 A1 | 5/2015 | Mulreed | |
| 2017/0196566 A1 | 7/2017 | Sgroi | |

FOREIGN PATENT DOCUMENTS

| | | |
|---|---|---|
| CN | 101669834 A | 3/2010 |
| CN | 101779974 A | 7/2010 |
| CN | 202982113 U | 6/2013 |
| CN | 202982114 U | 6/2013 |
| JP | 1980108347 A | 8/1980 |
| JP | 2000515049 A | 11/2000 |
| JP | 2009056306 A | 3/2009 |
| JP | 2011041798 A | 3/2011 |
| RU | 2447851 C2 | 4/2012 |
| WO | 2005023092 A2 | 3/2005 |

\* cited by examiner

CIRCULAR STAPLER AND STAPLE HEAD ASSEMBLY THEREOF

PRIORITY

This application is a continuation application and claims priority to U.S. patent application Ser. No. 14/655,350, filed on Jun. 25, 2015, which is the U.S. National Phase of International Application No. PCT/CN2013/090676, which in turn claims priority to Chinese Patent Applications Nos. 201220755800.0 and 201220755812.3, filed Dec. 29, 2012. The disclosures of all applications are incorporated herein by reference in their entirety.

TECHNICAL FIELD

The invention relates to a circular stapler and, more particularly, to a staple head assembly of a circular stapler, which belongs to the technical field of medical instrument.

BACKGROUND

It has been a history of more than 4,000 years for people to get the cognition of hemorrhoid. Up to now, the conventional methods for treating internal hemorrhoid include injection sclerotherapy, rubber band ligation and various kinds of surgical excisions. These methods are all treatments against the hemorrhoid per se and intended to make the hemorrhoid dwindled or disappeared. Among surgical excisions of hemorrhoid, a method named PPH surgery is to perform a procedure for prolapse and hemorrhoids with the assistance of a circular stapler.

U.S. Pat. No. 6,083,241 discloses a circular stapler, as shown in FIG. 1, its staple head assembly 40 includes an anvil 60 and a staple barrel 41 provided with a staple cartridge, a staple pusher and staples inside, and the anvil 60 and the staple barrel 41 are disposed oppositely. During surgery, the hemorrhoidal mucosa is pulled into the staple barrel 41 and is cut annularly while the anvil 60 and staple barrel 41 are stapling together. The opening on the housing of staple barrel 41 is significantly small, which can only be served to form a passageway 42 for string guiding instrument 140 to pass through the staple barrel 41 and to pull the purse-string sutured tissue into the staple barrel 41.

Currently, the staple barrel of commonly-used circular stapler, as the limitations in its structure, may provide limited viewing window and operating space for surgeon during the using process in surgery, which is bad for pulling-in operation on tissues. Besides, the accommodating space of staple barrel is also too limited to accommodate more to-be-excised tissues, which has great limitations, while a plurality of hemorrhoids need to be cut at one time in surgery (such as TST surgery against a plurality of hemorrhoids).

In addition, according to the clinical experience of surgeons, if an overlong tissue is pulled into the staple barrel, the postoperative performance may be not well. For example, it can be learned from medical knowledge that: a dentate annular line which can be seen at the commissure of anal canal skin and rectal mucosa and is enclosed by the edge of anal valves and the lower end of anal columns, is named dentate line. As the tissue structure above and below the dentate line are different, more than 85% of rectum and anus diseases occur near the dentate line. The dentate line is an induction area of defecation reflex, so when the excrement arrives at the anal canal via the rectum, the nerve terminal receptor at dentate line area will be stimulated and then make the anal canal open reflectively to discharge the excrement. If the tissues pulled in are too long to lead to excise dentate line in surgery, it will cause decreased defecation reflex on postoperative patient, which may make some adverse reactions such as constipation or sensory fecal incontinence occurred.

However, the conventional circular stapler only has scale indication for indicating the depth of stapler into anus on the surface of staple barrel (such as reference numeric 49 in FIG. 1), which can't provide criterion for surgeon to estimate the amount of hemorrhoid mucosa tissues pulled into staple barrel. As a result, the amount of mucosa tissues and the depth of tissues pulled into staple barrel cannot be determined, which may cause too many tissues pulled into staple barrel to make poor postoperative performance on patients.

SUMMARY

An object of the invention is to provide a circular stapler and the staple head assembly thereof, which can obtain large view window, large capacity and high operation convenience.

Another object of the invention is to provide a circular stapler and the staple head assembly thereof, which have the indicator function for indicating the depth of to-be-excised tissues pulled in to avoid too many tissues to be pulled in.

The object of the invention is realized by the technical solutions as follows:

A staple head assembly of circular stapler, comprising:

a staple barrel assembly including a staple barrel, a staple pusher piece arranged inside said staple barrel and a staple cartridge fixed at a distal end of said staple barrel; the distal end of said staple barrel assembly being a staple cartridge surface; said staple barrel comprising a tubular housing, an expansion-stopping tube disposed in said housing and a stiffener connected between said housing and said expansion-stopping tube; said housing being provided with a first cavity for accommodating to-be-excised tissues, and a proximal end of said housing being configured for connecting with a body of said circular stapler, and a distal end of said housing being configured for mounting said staple cartridge; wherein, at least one opening communicating with said first cavity is arranged on sidewall of said housing of staple barrel, and a distance from a distal end of said expansion-stopping tube to said staple cartridge surface is larger than that from a distal end of said opening to said staple cartridge surface, and at least a part of said first cavity is exposed from said opening; and an anvil assembly including an anvil ring and an anvil shaft which are fixedly connected to each other, said anvil shaft being capable of sliding in said expansion-stopping tube along a longitudinal direction.

Preferably, said housing comprises a first part with the distal end of housing and a second part with the proximal end of housing, and a diameter of said first part is larger than that of said second part, and a proximal end of said first part is connecting to a distal end of said second part in a tapered way.

Preferably, said housing of staple barrel is provided with a plurality of openings symmetrical about the longitudinal axis of said housing, and one said stiffener is correspondingly disposed between every two adjacent openings.

Preferably, in the cross-section of said housing of staple barrel, a circular arc length of said opening is larger than that of a connecting portion between two adjacent openings.

Preferably, the proximal end of said expansion-stopping tube extends to be close to the proximal end of said housing, and the proximal end of said anvil shaft which is adaptable with said expansion-stopping tube also extends to be close to the proximal end of said housing.

Preferably, the distance from the distal end of said expansion-stopping tube to said staple cartridge surface is less than that from the proximal end of said opening to said staple cartridge surface, and the distance from the proximal end of said expansion-stopping tube to said staple cartridge surface is larger than that from the proximal end of the opening to said staple cartridge surface.

Preferably, at least one guiding slot is arranged in a through-hole of said expansion-stopping tube, and said anvil shaft is provided with at least one guiding rib accordingly, which is capable of sliding in said guiding slot.

Preferably, said stiffener extends along the longitudinal direction from the proximal end of said expansion-stopping tube to beyond the distal end of said expansion-stopping tube and to be close to said staple cartridge.

Preferably, the shape of said staple pusher piece is made to be adaptable with said staple barrel, and a second cavity arranged inside said staple pusher piece is aligned with said first cavity of said staple barrel.

Preferably, said staple pusher piece comprises: a staple pusher ring at the distal end; a plurality of supporting plates extending along the longitudinal direction from said staple pusher ring to the proximal end in a tapered way; and a plurality of insertion sheets in long-stripe shape which are connected between two adjacent supporting plates and separated from each other; wherein said plurality of supporting plates are engaged with the corresponding said stiffeners and arranged to form said second cavity, and said plurality of insertion sheets in long-stripe shape are respectively inserted to an insertion space which is enclosed by said expansion-stopping tube, said housing and two adjacent stiffeners.

Preferably, the distance from the distal end of said insertion sheets to said staple cartridge surface is larger than that from the distal end of said opening to said staple cartridge surface, and at least a part of second cavity is exposed from said opening.

Preferably, the distance from the distal end of said opening to said staple cartridge surface is less than or equal to 32 mm.

Preferably, the distance from the distal end of said opening to said staple cartridge surface is larger than or equal to 20 mm, and less than or equal to 32 mm.

Preferably, the distance from the distal end of said opening to said staple cartridge surface is 30 mm.

Preferably, the distal end of said opening is provided with an indicator line.

A circular stapler, comprising a body and a staple head assembly connected with the distal end of said body, where the staple head assembly is as above described.

Compared with the prior art, beneficial effects of the embodiments of the invention mainly include:

1) by arranging opening(s) which can be communicating with the first cavity of the staple barrel in the staple barrel, with the distance from the distal end of the expansion-stopping tube to the staple cartridge surface being larger than that from the distal end of the opening(s) to the staple cartridge surface, at least a part of first cavity can be exposed from the opening(s), which can thusly not only provide a larger view window during surgery, but also facilitate the pulling-in operation on tissues and accommodate more to-be-excised tissues;

2) the distance from the distal end of the opening(s) of the staple barrel to the staple cartridge surface is less than or equal to 32 mm, which can thusly allow the surgeon to take the distal end of the opening(s) as a criterion determining the depth of tissues pulled in during surgery to avoid too long tissues pulled in to affect the surgery effect.

Figure 1:
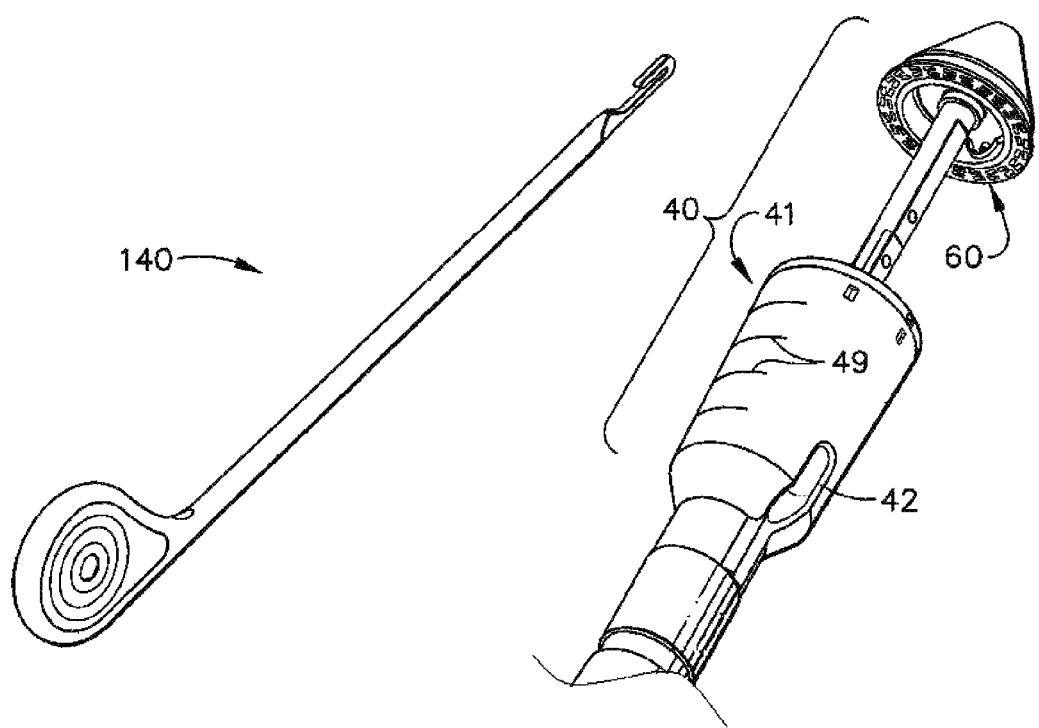
FIG. 1 is a perspective view of a circular stapler and a string guiding instrument in prior art.

Wherein, reference numerals are illustrated hereinbelow:
(The Invention)
body 1
staple head assembly 2
staple barrel assembly 3
staple barrel 31, 31'
tubular housing 311
first cavity 310、first part 311a、second part 311b、
distal end 311c、proximal end 311d
opening 313: distal end 313c、proximal end 313d、arc length 313a
connecting portion 314: arc length 314a
expansion-stopping tube 315
distal end 315c、proximal end 315d
through-hole 3151、guiding slot 3152
stiffener 316
insertion space 317
cartridge 32
staple cartridge surface 320
staple pusher piece 33、33'
second cavity 330
staple pusher ring 331
supporting plate 332、332' slot 3321, proximal edge 3322, 3322'
insertion sheet 333
anvil assembly 5
anvil ring 51
anvil shaft 52, guiding rib 521
to-be-excised hemorrhoid tissues 7
anoscope 8
indicator line 9
(Prior Art)
staple head assembly 40
anvil 60
staple barrel 41
passageway 42
string guiding instrument 140

DETAILED DESCRIPTION

Hereinafter, embodiments are described in detail with reference to the accompanying drawings. The term "distal end" and "proximal end" used in the description are described relative to the position of surgeon, wherein, the "distal end" is the end away from surgeon, and the "proximal end" is the end close to surgeon, which is opposite to the distal end.

The First Embodiment

Figure 2:
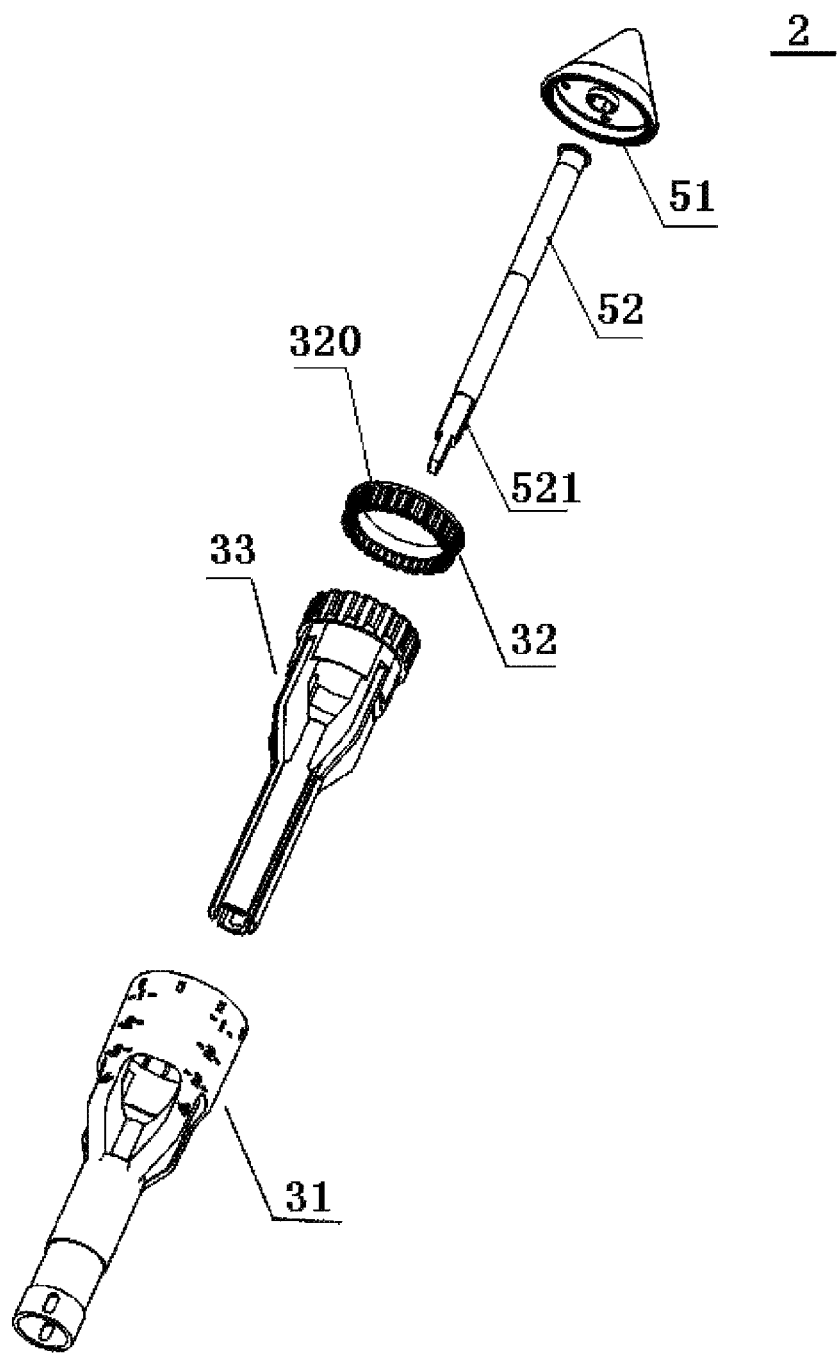
FIG. 2 is an exploded view of the staple head assembly of circular stapler provided by the first embodiment of the present invention.
Figure 3A:
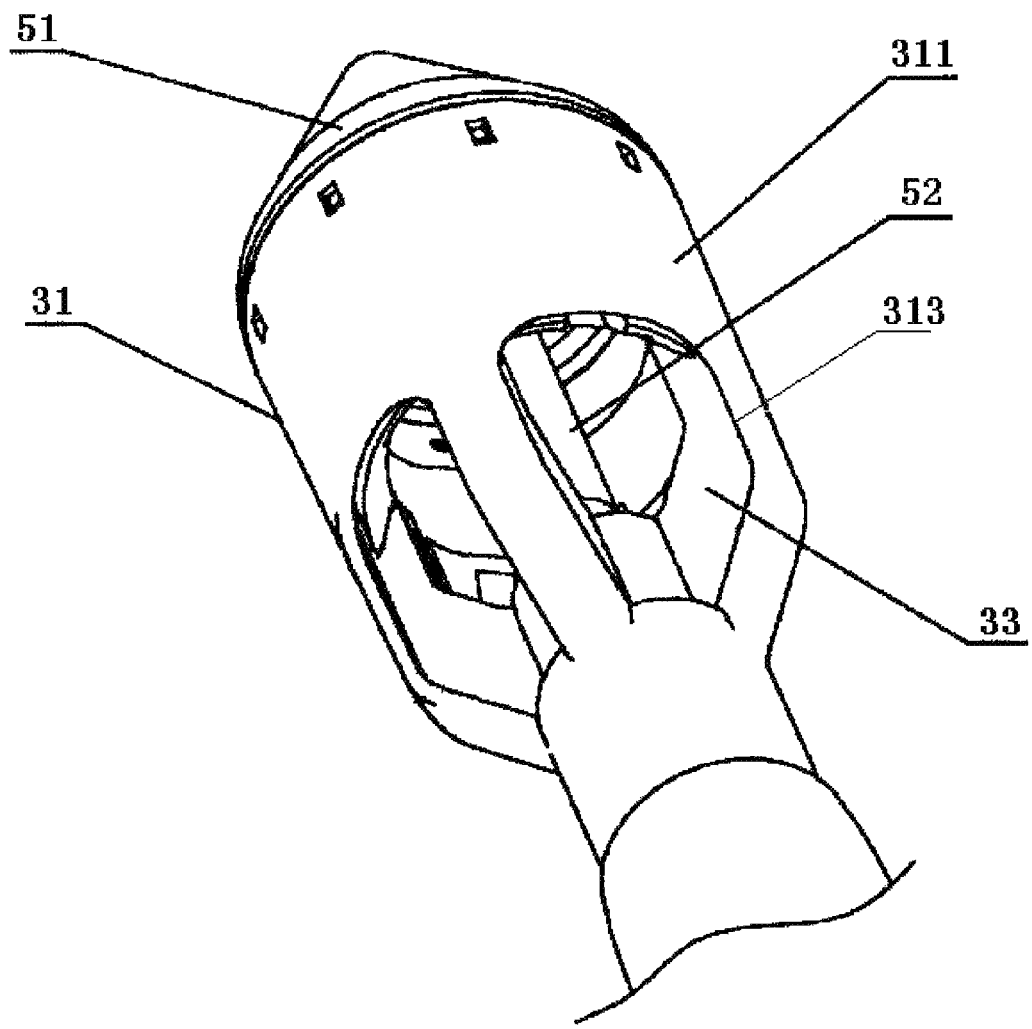
FIG. 3A is an assembled view of the staple head assembly of circular stapler provided by the first embodiment of the present invention.
Figure 3B:
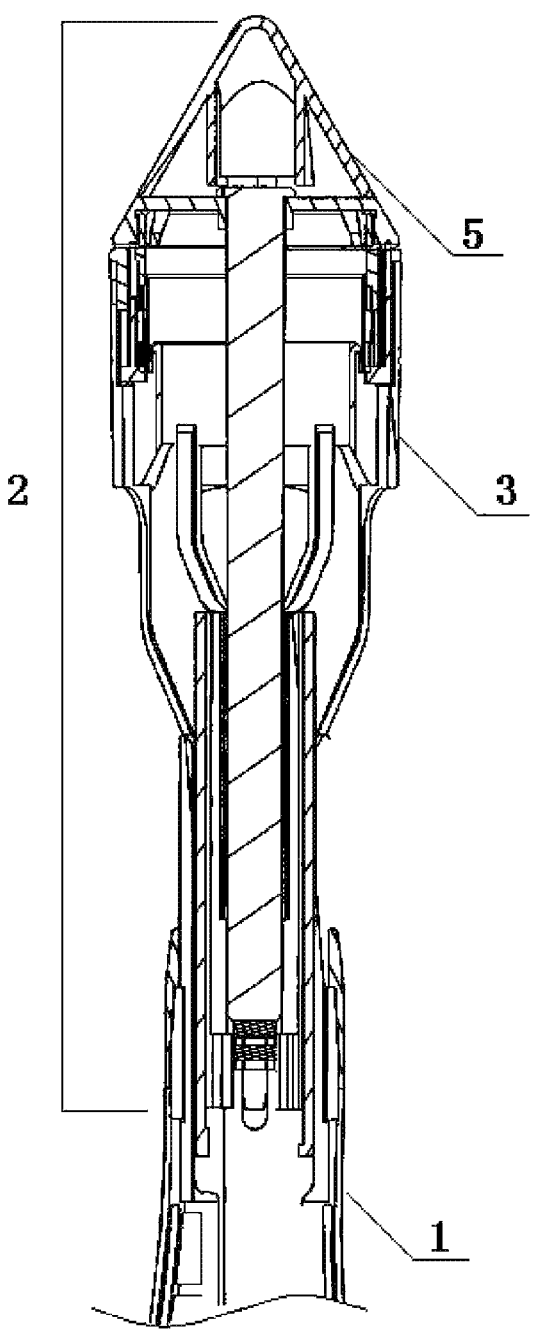
FIG. 3B is a sectional assembled view of the staple head assembly of circular stapler provided by the first embodiment of the present invention.

As shown in FIG. 2, FIG. 3A and FIG. 3B, a circular stapler, provided by the embodiment of the present invention, comprises a body 1, a first actuating mechanism (not shown) and a second actuating mechanism (not shown) which are arranged on the body 1, and a staple head assembly 2 connected to the distal end of body 1.

The staple head assembly 2 of the embodiment of the invention at least includes a staple barrel assembly 3 and an anvil assembly 5 which are disposed oppositely. The anvil assembly 5 includes an anvil ring 51 and an anvil shaft 52 which are fixedly connected to each other. The anvil assembly 5 may be driven by the first actuating mechanism (not shown) to move along the longitudinal direction of circular stapler relative to the staple barrel assembly 3, between a first position away from the staple barrel assembly 3 and a second position close to the staple barrel assembly 3. When the anvil assembly 5 is in the first position, it is convenient for pulling the to-be-excised tissues into the staple barrel 31, and when the anvil assembly 5 is in the second position, the tissues in the staple barrel 31 can be stapled and excised.

The staple barrel assembly 3 at least includes a staple barrel 31, a staple cartridge 32 fixed at the distal end of staple barrel 31, and a staple pusher piece 33 arranged inside the staple barrel 31. The staple pusher piece 33 moves along the longitudinal direction of circular stapler with the function of the second actuating mechanism, to fire the staples in staple cartridge 32 to the to-be-excised tissues in staple barrel 31, which can get the tissues stapled and sutured. The staple cartridge 32 is fixed at the distal end of staple barrel 31, thereby the distal end surface of the staple barrel assembly 3 is the staple cartridge surface 320, which is disposed oppositely as to the anvil ring 51.

As shown in FIG. 4A to FIG. 4F, the staple barrel 31 includes a tubular housing 311, a expansion-stopping tube 315 disposed in the tubular housing 311 and a stiffener 316 connected between the tubular housing 311 and the expansion-stopping tube 315. Preferably, in this embodiment, the tubular housing 311, the expansion-stopping tube 315 and the stiffener 316 are integrally molded.

The housing 311 includes a first cavity 310 for accommodating the to-be-excised tissues. The distal end 311c of housing 311 is configured for mounting the staple cartridge 32, and the proximal end 311d of housing 311 is configured for connecting the body 1 of circular stapler. Preferably, in this embodiment, the housing 311 includes a first part 311a provided with the distal end 311c of housing and a second part 311b provided with the proximal end 311d of housing. The diameter of the first part 311a is larger than that of the second part 311b, and the proximal end of the first part 311a is connected to the distal end of the second part 311b in a tapered way.

Figure 4A:
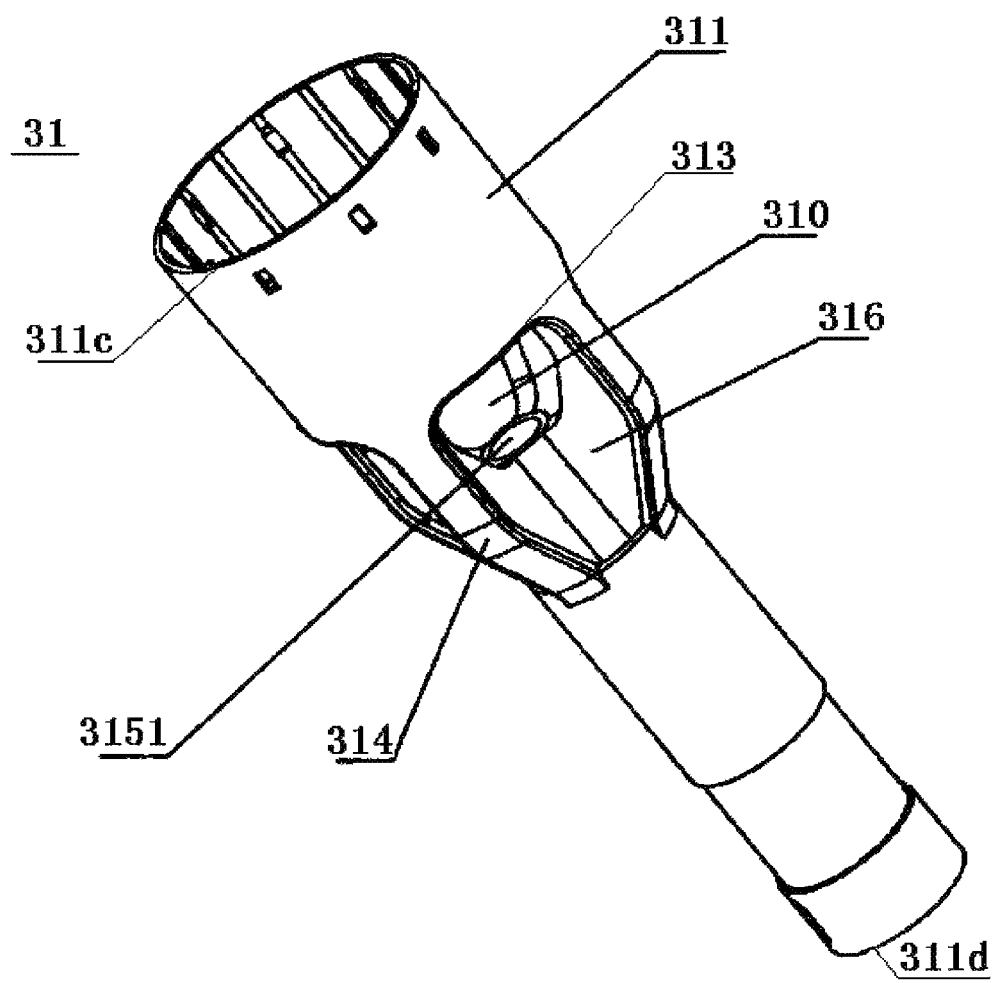
FIG. 4A is a perspective view of the staple barrel provided by the first embodiment of the present invention.
Figure 4B:
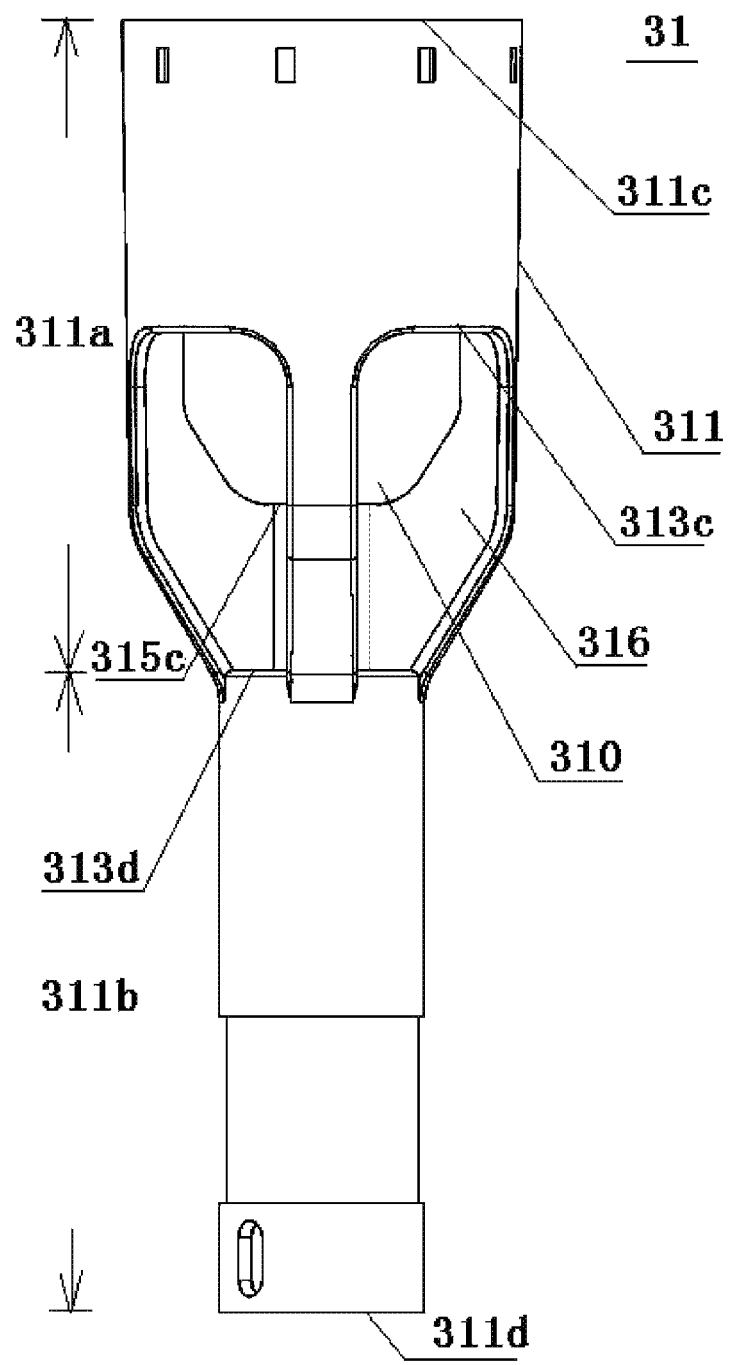
FIG. 4B is a front view of the staple barrel provided by the first embodiment of the present invention.
Figure 4C:
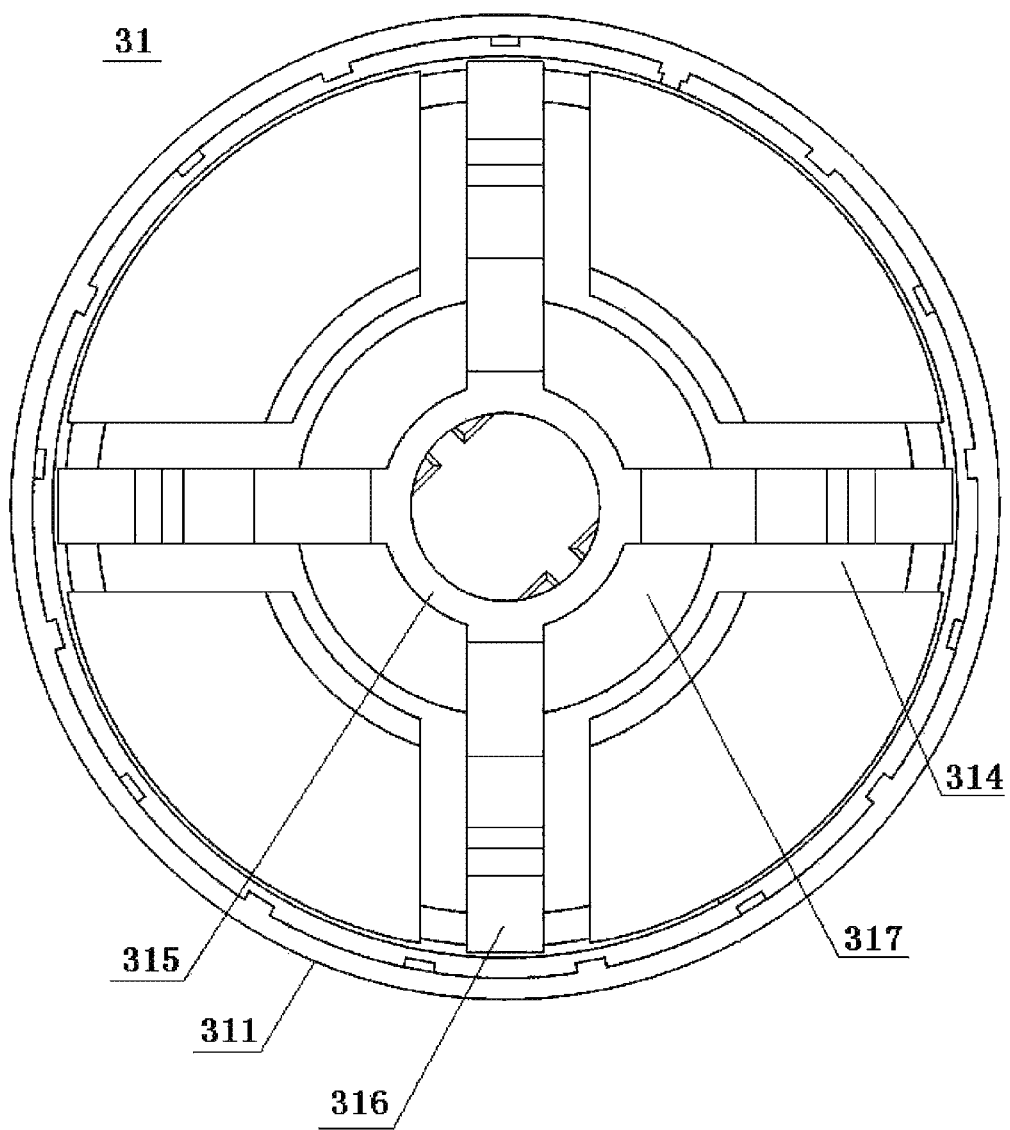
FIG. 4C is a top view of the staple barrel provided by the first embodiment of the present invention.
Figure 4D:
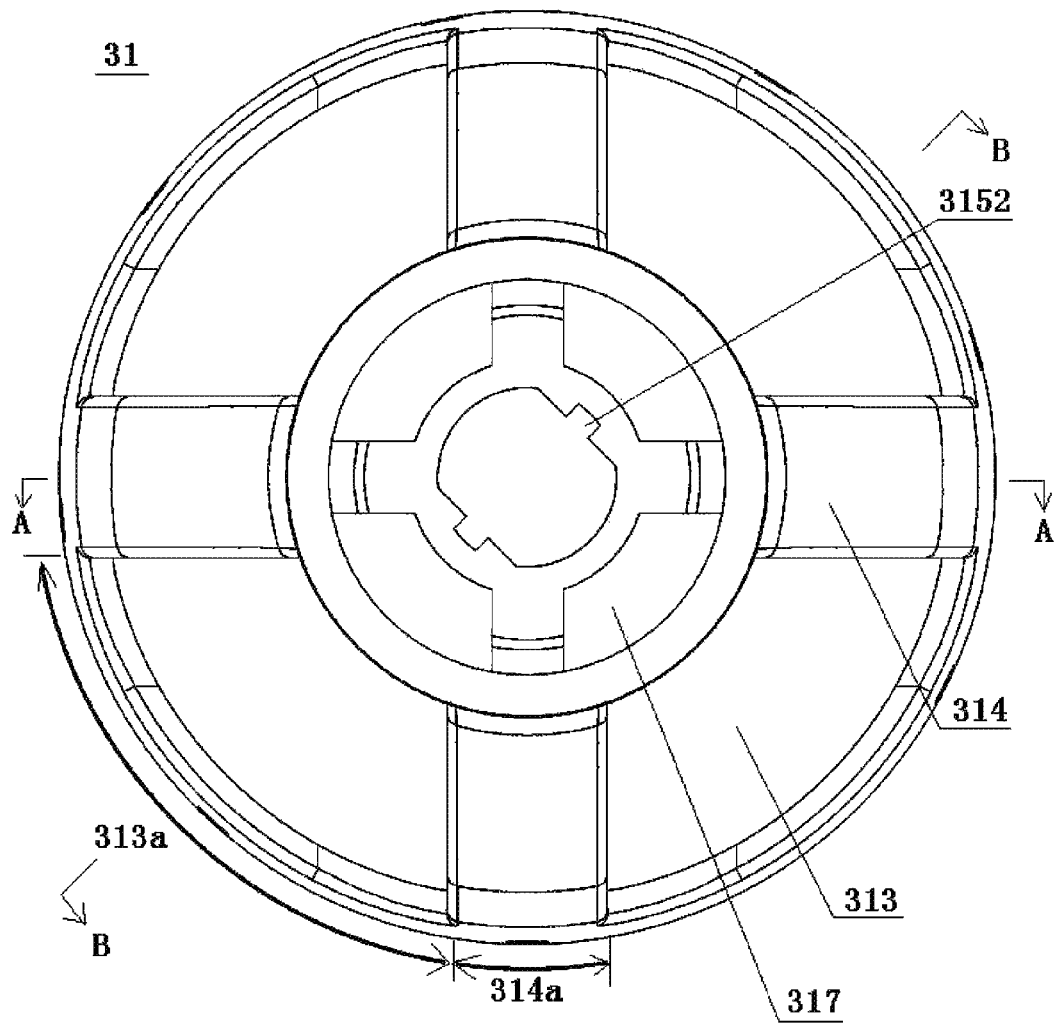
FIG. 4D is a bottom view of the staple barrel provided by the first embodiment of the present invention.

At least one opening 313 communicating with the first cavity 310 is arranged on the sidewall of said housing 311, which is for surgeons to observe the situation of tissues pulled-in. Preferably, in this embodiment, the sidewall of housing 311 of staple barrel 31 is provided with four openings 313 symmetrical about the longitudinal axis of housing 311, as a result that the openings 313 in four directions may provide better multi-direction windows for medical workers during surgery. Of course, the amount of openings 313 are not limited thereof, and it may also be one, two, three or more. In the cross-section of the housing of the staple barrel 31, the circumferential arc length 313a corresponding to the opening 313 is larger than the circumferential arc length 314a corresponding to the connecting portion 314 between two adjacent openings. Thus, such large openings may provide the surgeon excellent viewing angle during surgery. Preferably, in this embodiment, as shown in FIG. 4B and FIG. 4D, the circumferential arc length corresponding to each opening 313 is roughly equal to ¼ of circumferential length of the housing 311.

Figure 4E:
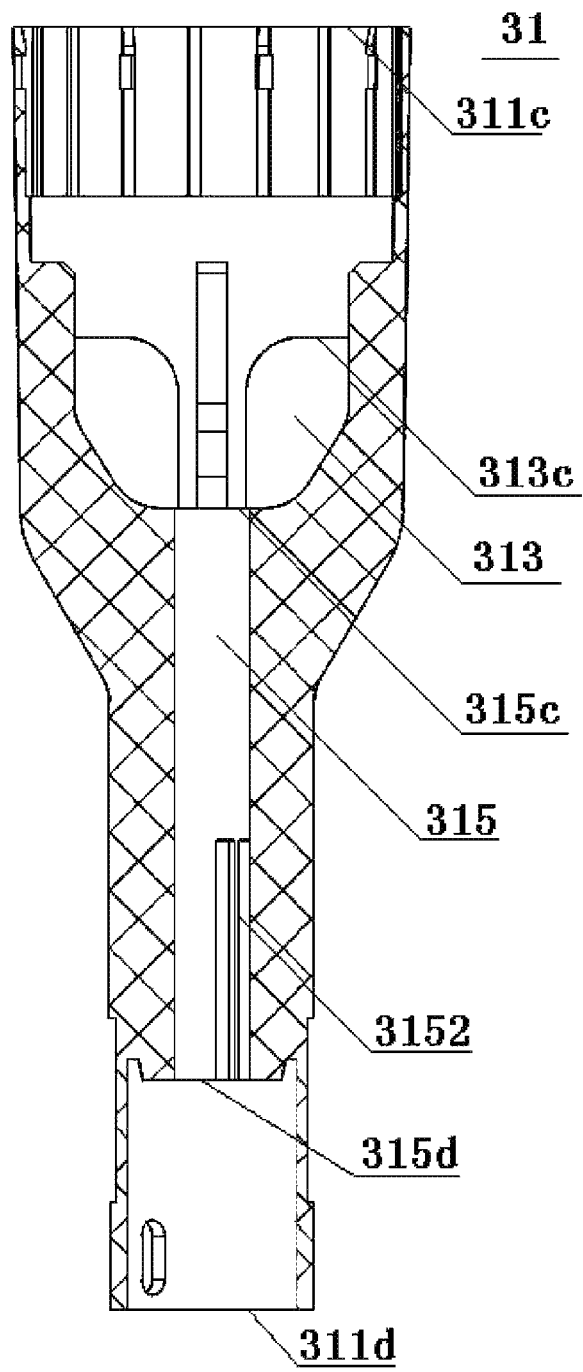
FIG. 4E is a A-A sectional view of the staple barrel provided by the first embodiment of the present invention.
Figure 4F:
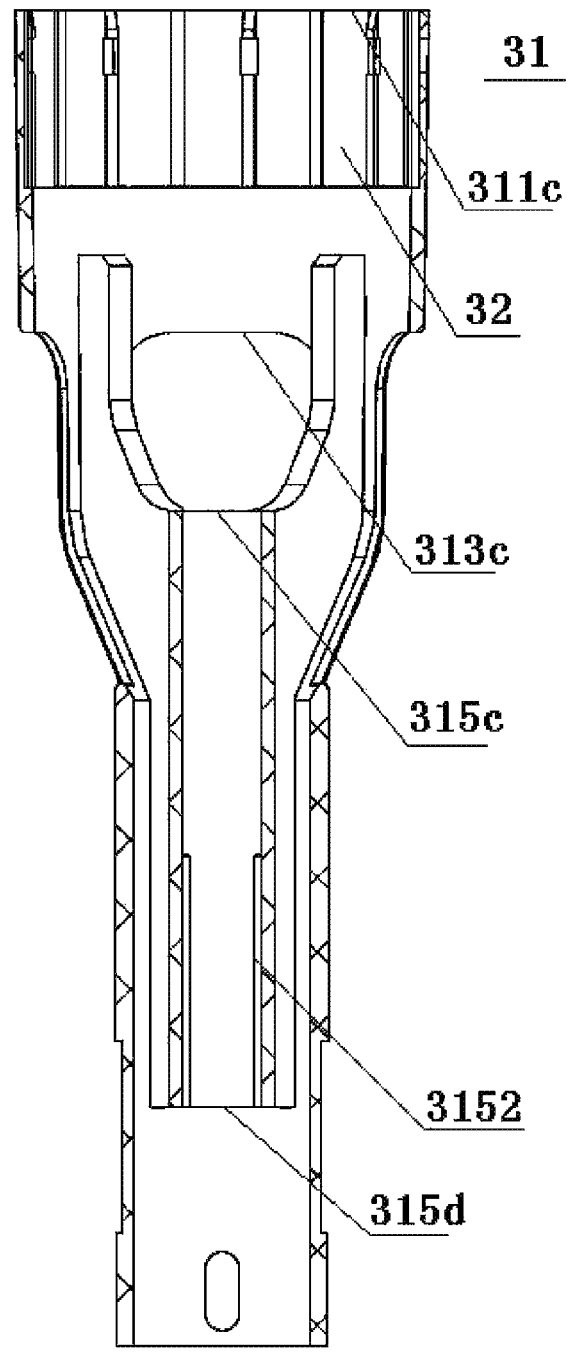
FIG. 4F is a B-B sectional view of the staple barrel provided by the first embodiment of the present invention.

The expansion-stopping tube 315 includes a through-hole 3151 to allow the anvil shaft 52 of anvil assembly 5 to slide through. In a preferred embodiment, the through-hole 3151 of expansion-stopping tube 315 is disposed with two guiding slots 3152 therein (as shown in FIG. 4D and FIG. 4E), and the anvil shaft 52 is provided with two guiding ribs 521 (as shown in FIG. 2), each of which may slide in the corresponding guiding slots 3152. The number of pairs of guiding slot and guiding rib may be not limited to two, and it can be one or more than two. To accommodate more to-be-excised tissues within the housing 311 and provide larger operating space for the instruments such as the string guiding instrument to facilitate the pulling-in operation of tissues, the distance from the distal end 315c of expansion-stopping tube 315 to the staple cartridge surface 320 is larger than that from the distal end 313c of opening 313 to the staple cartridge surface 320, that is to say, the distance from the distal end 315c of expansion-stopping tube 315 to the proximal end 311d of housing 311 is less than that between the farthest edge (that is the distal end) 313c of opening 313 and the proximal end 311d of housing 311, thus at least a part of first cavity 310 is exposed from the opening 313. Preferably, in this embodiment, the distance from the distal end 315c of expansion-stopping tube 315 to the staple cartridge surface 320 is less than that from the proximal end 313d of opening 313 to the staple cartridge surface 320, and the distance from the proximal end 315d of expansion-stopping tube 315 to the staple cartridge surface 320 is larger than that from the proximal end 313d of opening 313 to the staple cartridge surface 320. Such structure is benefit for the sliding stability of the anvil shaft 52 sliding in the expansion-stopping tube 315 along a longitudinal direction. However, the invention is not limited thereto, for example, the expansion-stopping tube in whole may also correspond to the second part of the housing, that is the distance from the distal end of expansion-stopping tube to the staple cartridge surface is larger than that from the proximal end of opening to the staple cartridge surface.

Both the distal ends of the stiffener 316 and the expansion-stopping tube 315 in present invention are relatively lower than those in prior art in which both the distal ends of stiffener and expansion-stopping tube are close to the staple cartridge surface. To compensate for shortage in axial and circumferential strength resulted by lowering of expansion-stopping tube 13, the proximal end 315d of expansion-stopping tube 315 in the invention is made to extend as compared with that in prior art, and also the anvil shaft 52 is lengthened (which equals to an extension of proximal end) to increase the adaptation and connection between the anvil shaft 52 and the expansion-stopping tube 315. To be specific, the proximal end 315d of expansion-stopping tube 315 extends to be close to the proximal end 311d of housing 311, and the proximal end of anvil shaft 52 being adaptable with the expansion-stopping tube 315 also extends to be close to the proximal end 311d of the housing 311.

The stiffener 316 is mainly served for connecting the tubular housing 311 and the expansion-stopping tube 315. In this preferred embodiment, since the housing 311 is provided with a plurality of openings 313, a long-plane-shaped stiffener 316 can be arranged correspondingly on the inner wall of the connecting portion 314 which is mounted between two adjacent openings on the housing 311, to fix the expansion-stopping tube 315 in the housing 311 correspondingly. Among the expansion-stopping tube 315, the housing 311 and two adjacent stiffeners 316, there is an insertion space 317 enclosed (as shown in FIG. 4C) for the insertion sheet 333 of the staple pusher piece 33 (illustrated hereinafter) to insert into. In this preferred embodiment, the stiffener 316 extends from the proximal end 315d of the expansion-stopping tube 315 along the longitudinal direction to beyond the distal end 315c of expansion-stopping tube 315, and to get close to the staple cartridge 32. That is, the proximal end of stiffener 316 is basically aligned with the proximal end 315d of expansion-stopping tube 315, however the distal end of the stiffener 316 extends to be more close to the staple cartridge surface 320 than the distal end 313c of the opening 313. Such arrangement is benefit for improving the strength of the housing 311 of staple barrel 31. The amount, length and placement of the stiffeners may be varied in many ways. For example, each stiffener may be placed on the outer wall of the expansion-stopping tube continuously or discontinuously.

Figure 5A:
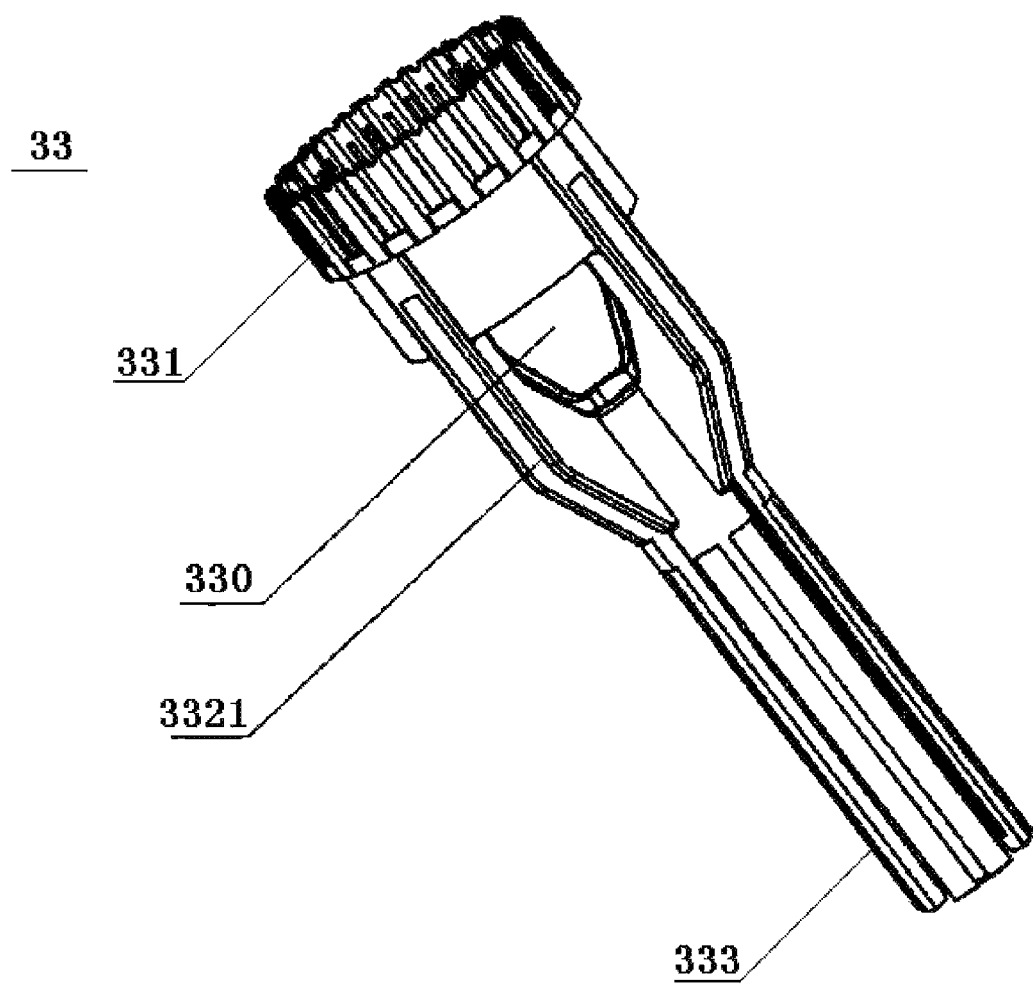
FIG. 5A is a perspective view of the staple pusher piece provided by the first embodiment of the present invention.
Figure 5B:
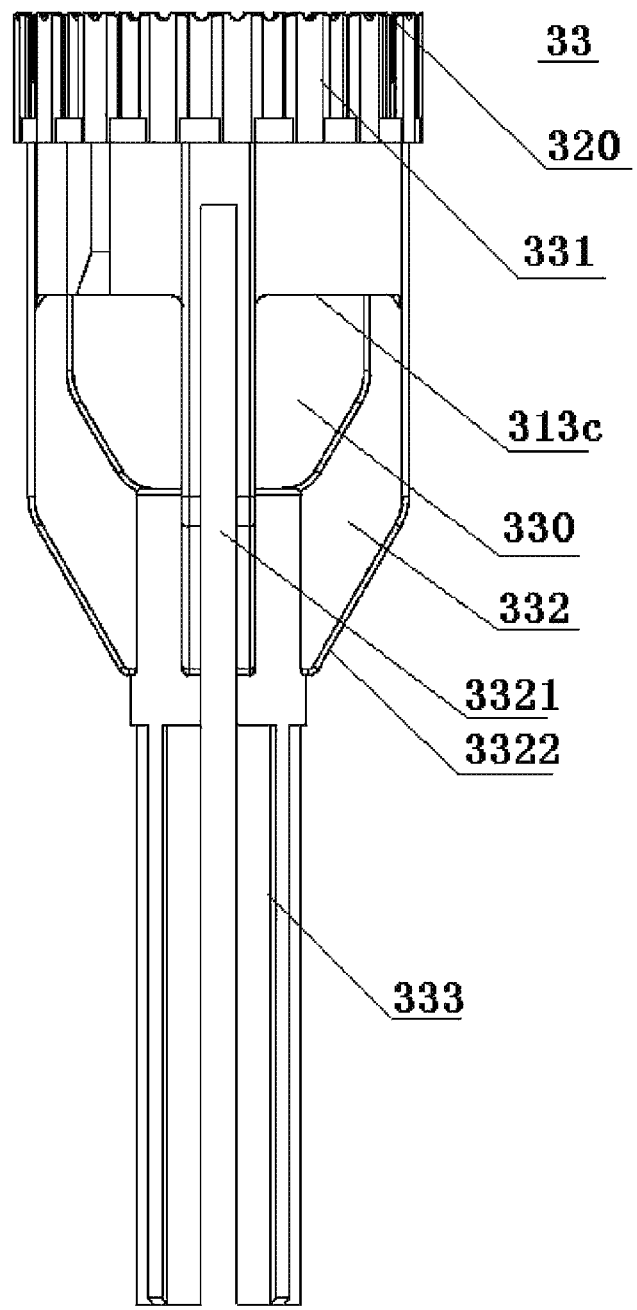
FIG. 5B is a front view of the staple pusher piece provided by the first embodiment of the present invention.
Figure 5C:
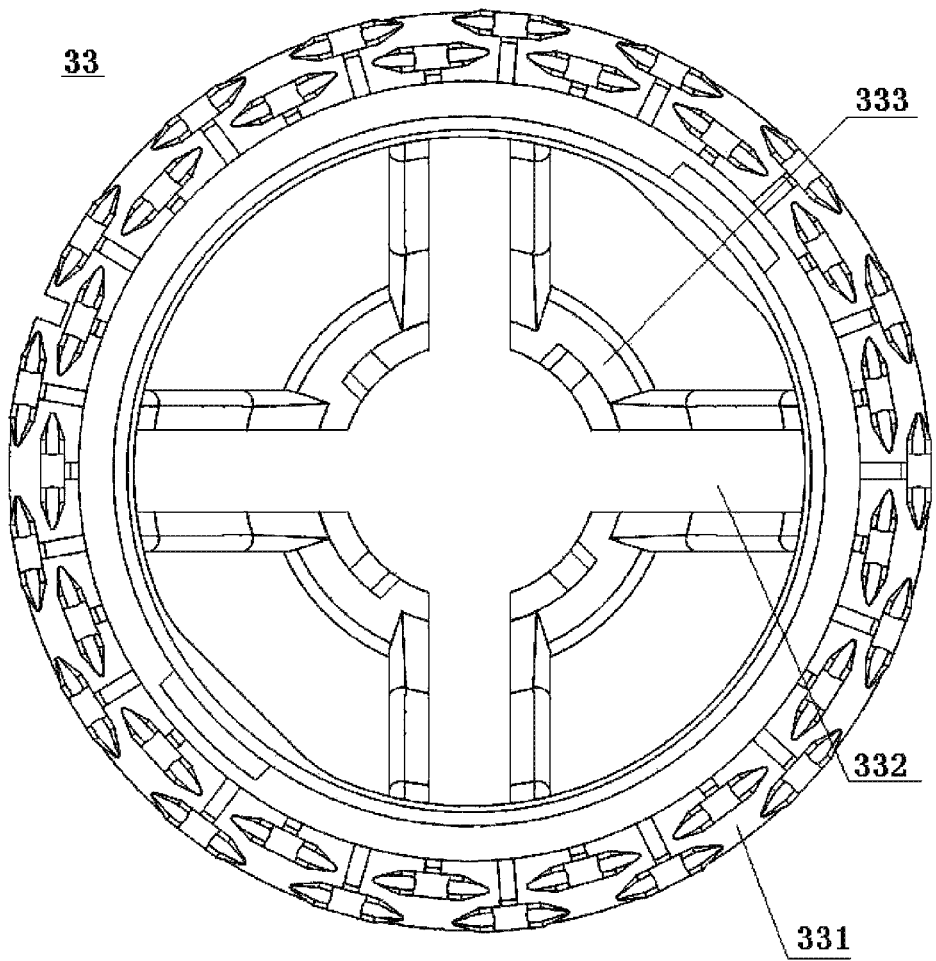
FIG. 5C is a top view of the staple pusher piece provided by the first embodiment of the present invention.

As shown in FIG. 5A to FIG. 5C, the shape of staple pusher piece 33 may be made to match with the staple barrel 31. Specifically, the staple pusher piece 33 includes: a staple pusher ring 331 at the distal end, a plurality of supporting plates 332 extending from the staple pusher ring 331 to the proximal end along the longitudinal direction in a tapered way, and a plurality of long-striped insertion sheet 333 connected between two adjacent supporting plates 332 and separated from each other. In the staple pusher piece 33, there is a second cavity 330 (that is an inner space which is formed by being embraced with a plurality of supporting plates 332), which is aligned to the first cavity 310 of staple barrel 31. A plurality of long-striped insertion sheet 333 are inserted into the insertion space 317 of staple barrel 31 to form a tubular like structure surrounding around the periphery of expansion-stopping tube 315. In this preferred embodiment, to accommodate more to-be-excised tissues and provide larger operating space for the instrument such as the string guiding instrument to facilitate the pulling-in operation of tissues, similar with the corresponding structure of expansion-stopping tube 315, the distance from the distal end of insertion sheet 333 to the staple cartridge surface 320 is larger than that from the distal end of opening 313 to the staple cartridge surface 320, and at least a part of second cavity 330 is exposed from the opening 313.

Each supporting plate 332 corresponds to each stiffener 316 in the staple barrel 31, and each supporting plate 332 is provided with a slot 3321 capable of engaging on the outside surface of the stiffener 316 correspondingly. The engaging way between the stiffener and the supporting plate may be changed to: the stiffener of the staple barrel is provided with a slot, and the supporting plate of staple pusher piece can be engaged into the slot of the stiffener. The engaging fixation way between the stiffener and the supporting plate is benefit for improving the stableness of the staple pusher piece 33 in the staple barrel 31. Obviously, the stiffener and the supporting plate may employ other fixation way. In addition, in this embodiment, after the supporting plate 332 of staple pusher piece 33 and the stiffener 316 of staple barrel 31 are assembled, the proximal edge 3322 of the supporting plate 332 abuts against the inner side of the housing 311 of staple barrel 31.

Figure 6:
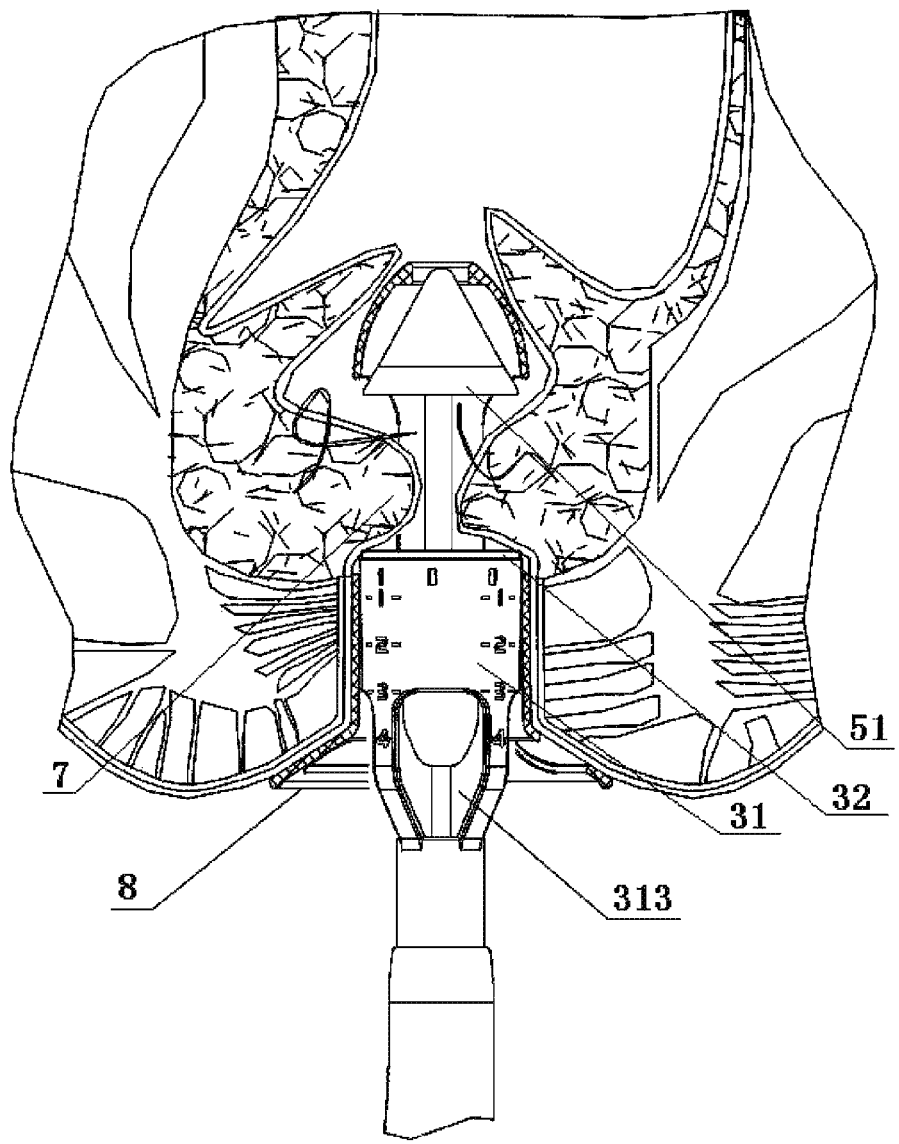
FIG. 6 is a schematic diagram showing the operational state of the staple head assembly in surgery provided by the first embodiment of the present invention.

Hereinafter, taking the surgery of excising hemorrhoid tissues for example, the operating method of the circular stapling instrument in this embodiment of the invention will be illustrated with FIG. 6 as: after a purse-string suture is performed on the to-be-excised hemorrhoid tissues 7, place the circular stapler which is under the condition that the anvil ring 51 and the staple cartridge 32 are far away from each other into an anoscope 8; afterwards, apply the string guiding instrument to insert into the space between the anvil ring 51 and the staple cartridge 32 from the opening 313 of staple barrel 31 and to pull the purse string to get the to-be-excised hemorrhoid tissues 7 pulled into the accommodating space (the first cavity and the second cavity) of circular stapler; and then, adjust the first actuating mechanism of circular stapler to make the distance from the staple cartridge 32 to the anvil ring 51 reduced until the anvil ring 51 and the staple cartridge 32 clap the to-be-excised hemorrhoid tissues 7 tightly; subsequently, operate the second actuating mechanism of circular stapler and fire the staple in the staple cartridge 32 to the tissues by using the staple pusher piece 33 to perform stapling and suturing and to excise the tissues at the same time. The application of the circular stapler in this embodiment of the invention is not limited to excise the hemorrhoid tissues, but also may be used to excise other tissues in the anorectal surgery.

Second Embodiment

Figure 7:
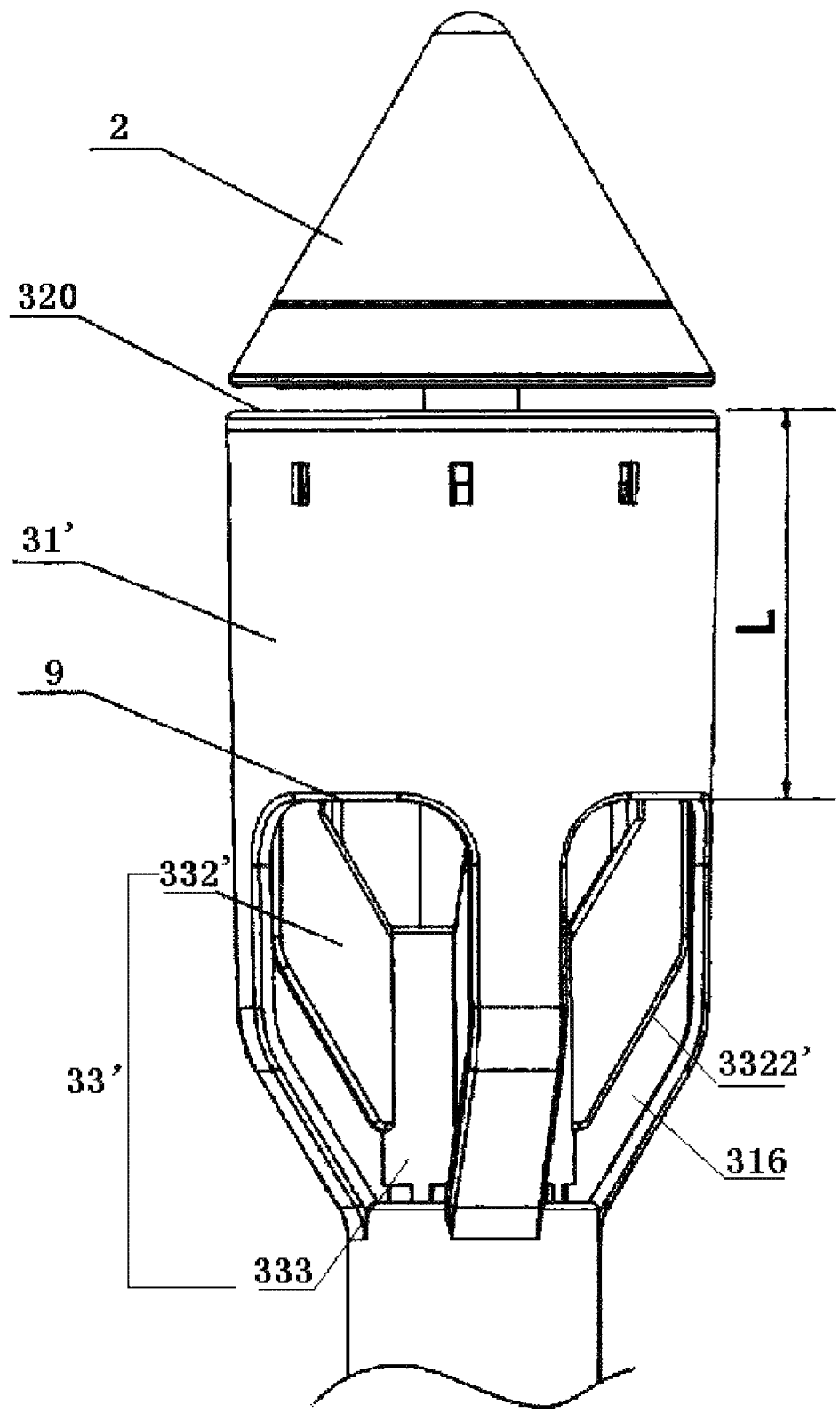
FIG. 7 is a perspective view of the staple head assembly provided by the second embodiment of the present invention.

As shown in FIG. 7, one difference from the first embodiment is, in the staple barrel 31' of second embodiment, one end of opening 313 (the distal end or edge of opening) close to the staple cartridge surface 320 is provided with an indicator line 9, which is convenient for the surgeon with different models of circular stapler to get to know the value of distance L from the distal end of opening to the staple cartridge surface. The distance L from the indicator line 9 to the staple cartridge surface 320 may be, for example, greater than or equal to 20 mm, and less than or equal to 32 mm, and preferable it can be 30 mm to obtain the best clinical effect. The indicator line 9 may be realized in various ways, which includes directly printing the indicator line at the opening of the staple barrel 31' and marking the corresponding distance value such as 20 mm, 30 mm or 32 mm and so on. Thusly, before the surgery, the surgeon may know the distance from the opening to the staple cartridge surface in such stapler according to the value indicated by the indicator line 9. During the operation process of surgery, the doctor may take the distal end of opening in the staple barrel as a criterion determining the depth of tissues pulled in to avoid too long tissues pulled in to affect the surgery effect.

The other difference from the first embodiment is, the proximal edge 3322' of supporting plate 332' of staple pusher piece 33' may not abut against the housing 311 of staple barrel 31'.

The above description only illustrates preferred embodiments of the invention, which can't be used for limiting the scope of the invention. Therefore, any other equivalent deformations or modifications without departing from the spirit of the invention are intended to be included in the scope of invention.

The invention claimed is:

1. A staple head assembly of a circular stapler, comprising:
    a staple barrel assembly including a staple barrel, a staple pusher piece arranged inside said staple barrel and a staple cartridge fixed at a distal end of said staple barrel; the distal end of said staple barrel assembly being a staple cartridge surface; said staple barrel comprising a tubular housing, an expansion-stopping tube disposed in said housing and at least one stiffener connected between said housing and said expansion-stopping tube; said housing being provided with a first cavity for accommodating to-be-excised tissues and a second cavity, an inner space formed by being embraced with a plurality of supporting plates of said staple pusher piece and arranged inside said staple pusher piece, aligned with said first cavity of said staple barrel;
    a proximal end of said housing configured for connecting with a body of said circular stapler, and a distal end of said housing configured for mounting said staple cartridge; and
    at least one opening, communicating with said first cavity and said second cavity, arranged on a sidewall of said housing of said staple barrel, wherein a distance from a distal end of said expansion-stopping tube to said staple cartridge surface is larger than that from a distal end of said opening to said staple cartridge surface,
    wherein the supporting plates are extended along a longitudinal direction from a distal end to the proximal end of said staple pusher piece in a tapered way.

2. The staple head assembly according to claim 1, wherein said housing comprises a first part with the distal end of said housing and a second part with the proximal end of said housing, and a diameter of said first part is larger than that of said second part, and a proximal end of said first part is connecting to a distal end of said second part in a tapered way.

3. The staple head assembly according to claim 1, wherein said housing of said staple barrel is provided with a plurality of openings symmetrical about a longitudinal axis of said housing, and one of said stiffener is correspondingly disposed between every two adjacent openings.

4. The staple head assembly according to claim 3, wherein, in the cross-section of said housing of said staple barrel, a circular arc length of said opening is larger than that of a connecting portion between two adjacent openings.

5. The staple head assembly according to claim 1, wherein the distance from the distal end of said expansion-stopping tube to said staple cartridge surface is less than that from the proximal end of said opening to said staple cartridge surface, and the distance from the proximal end of said expansion-stopping tube to said staple cartridge surface is larger than that from the proximal end of the opening to said staple cartridge surface.

6. The staple head assembly according to claim 1, wherein at least one guiding slot is arranged in a through-hole of said expansion-stopping tube, and an anvil shaft is provided with at least one guiding rib accordingly which is capable of sliding in the at least one guiding slot.

7. The staple head assembly according to claim 1, wherein said stiffener extends along the longitudinal direction from a proximal end of said expansion-stopping tube to beyond the distal end of said expansion-stopping tube and to be close to said staple cartridge.

8. The staple head assembly according to claim 1, wherein a proximal edge of a supporting plate of the staple pusher piece is not abutted against the housing of said staple barrel.

9. The staple head assembly according to claim 1, wherein said plurality of supporting plates is engaged with the corresponding said stiffeners.

10. The staple head assembly according to claim 1, wherein a distance from a distal end of a insertion sheet to said staple cartridge surface is larger than that from the distal end of said opening to said staple cartridge surface, and at least a part of said second cavity is exposed from said opening.

11. The staple head assembly according to claim 1, wherein the distance from the distal end of said opening to said staple cartridge surface is less than or equal to 32 mm.

12. The staple head assembly according to claim 11, wherein the distance from the distal end of said opening to said staple cartridge surface is larger than or equal to 20 mm, and less than or equal to 32 mm.

13. The staple head assembly according to claim 12, wherein the distance from the distal end of said opening to said staple cartridge surface is 30 mm.

14. The staple head assembly according to claim 1, wherein the distal end of said opening is provided with an indicator line for indicating a distance value from the distal end of said opening to said staple cartridge surface.

15. The staple head assembly according to claim 1, wherein a proximal end of said stiffener is aligned with a proximal end of said expansion-stopping tube and said distal end of the stiffener extends and is more close to the staple cartridge surface than the distal end of the opening.

* * * * *